United States Patent
Laufer

Patent Number: 5,989,284
Date of Patent: Nov. 23, 1999

[54] METHOD AND DEVICE FOR SOFT TISSUE MODIFICATION

[75] Inventor: Michael D. Laufer, Menlo Park, Calif.

[73] Assignee: Hearten Medical, Inc., Tustin, Calif.

[21] Appl. No.: 08/801,998

[22] Filed: Feb. 18, 1997

[51] Int. Cl.[6] .................................................. A61F 7/00
[52] U.S. Cl. ................................. 607/96; 607/98
[58] Field of Search .................. 600/16, 17, 18; 607/96, 98, 99, 100, 101; 604/96; 128/898

[56] References Cited

U.S. PATENT DOCUMENTS

| | | | |
|---|---|---|---|
| 4,765,331 | 8/1988 | Petruzzi et al. | |
| 4,807,620 | 2/1989 | Strul et al. | |
| 4,865,047 | 9/1989 | Chou et al. | |
| 5,057,106 | 10/1991 | Kasevich et al. | 606/33 |
| 5,103,804 | 4/1992 | Abele et al. | |
| 5,114,423 | 5/1992 | Kasprzyk et al. | 606/27 |
| 5,230,349 | 7/1993 | Langberg | |
| 5,246,438 | 9/1993 | Langberg | 606/33 |
| 5,261,878 | 11/1993 | Galindo | 604/96 |
| 5,295,955 | 3/1994 | Rosen et al. | 604/22 |
| 5,303,719 | 4/1994 | Wilk et al. | 128/898 |
| 5,304,169 | 4/1994 | Sand | 606/5 |
| 5,314,466 | 5/1994 | Stern et al. | 607/156 |
| 5,370,677 | 12/1994 | Rudie et al. | 607/101 |
| 5,370,678 | 12/1994 | Edwards et al. | 607/101 |
| 5,405,346 | 4/1995 | Grundy et al. | 606/41 |
| 5,431,646 | 7/1995 | Vassiliadis et al. | 606/6 |
| 5,437,664 | 8/1995 | Cohen et al. | 606/42 |
| 5,447,529 | 9/1995 | Marchlinski et al. | 607/99 |
| 5,454,807 | 10/1995 | Lennox et al. | 606/15 |
| 5,454,809 | 10/1995 | Janssen | 606/41 |
| 5,458,596 | 10/1995 | Lax et al. | 606/31 |
| 5,484,432 | 1/1996 | Sand | 606/5 |
| 5,498,260 | 3/1996 | Rink et al. | 606/16 |
| 5,522,873 | 6/1996 | Jackman et al. | 607/122 |
| 5,529,067 | 6/1996 | Larsen et al. | |
| 5,540,679 | 7/1996 | Fram et al. | 606/27 |
| 5,545,195 | 8/1996 | Lennox et al. | 607/105 |

*Primary Examiner*—Linda C. M. Dvorak
*Assistant Examiner*—Rosiland Kearney
*Attorney, Agent, or Firm*—Burns, Doane, Swecker & Mathis LLP

[57] ABSTRACT

A device and method for shortening the chordae tendineae by heating them. Shortening the chordae tendineae stabilizes the atrioventricular valve to which they are attached, thus reducing or halting valve prolapse. A catheter having a heating tip system is inserted in the heart of a patient and maneuvered by an operating surgeon so that the heating tip can induce or transfer heat to the chordae tendineae. The heating tip system heats the chordae tendineae by direct transmission of heat or by inducing heat in the chordae tendineae with electromagnetic radiation. The operating surgeon monitors the heating of the chordae tendineae and when the desired degree of shorting has been achieved, the catheter is removed from the patient.

26 Claims, 10 Drawing Sheets

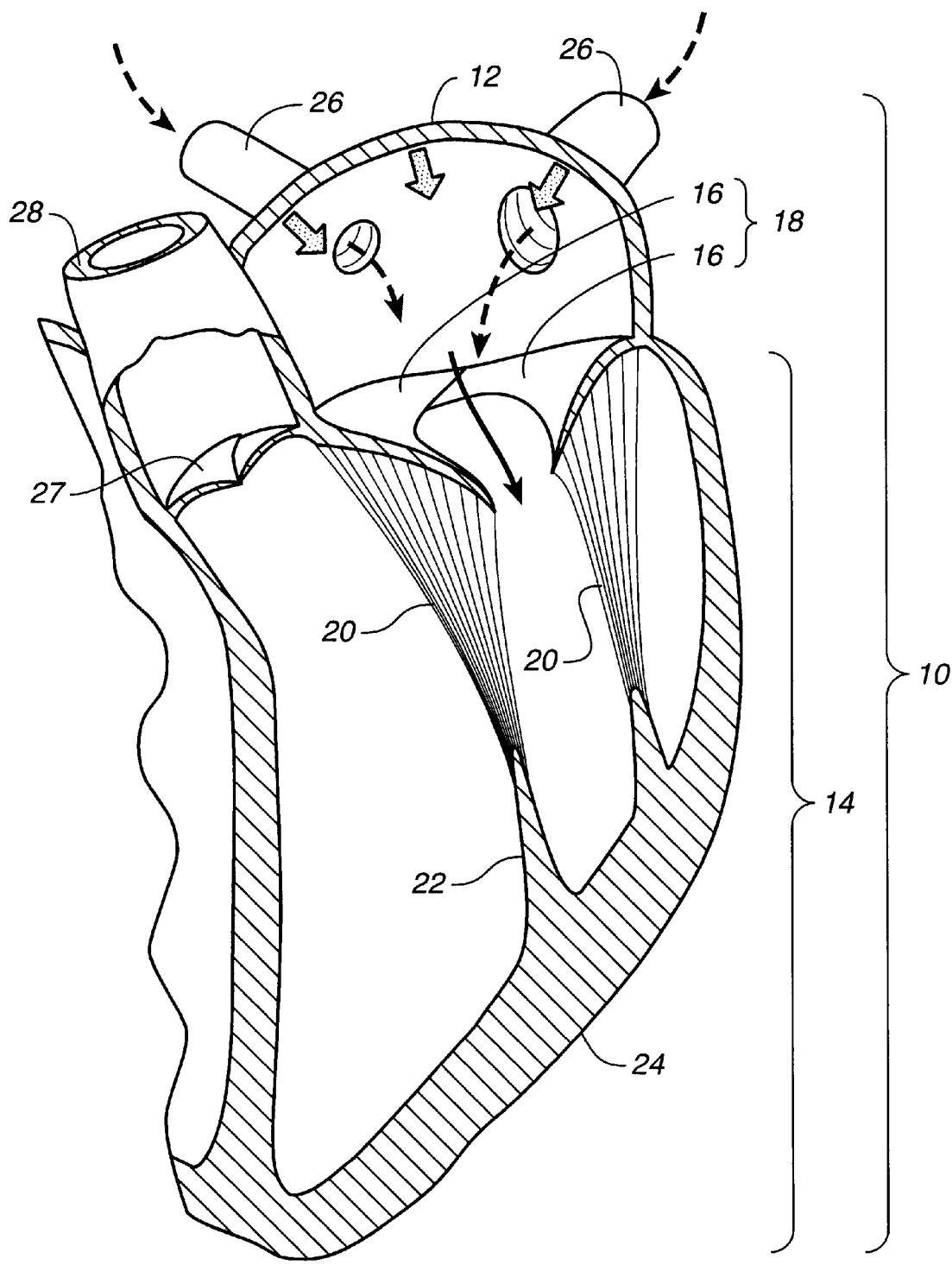
FIG._1

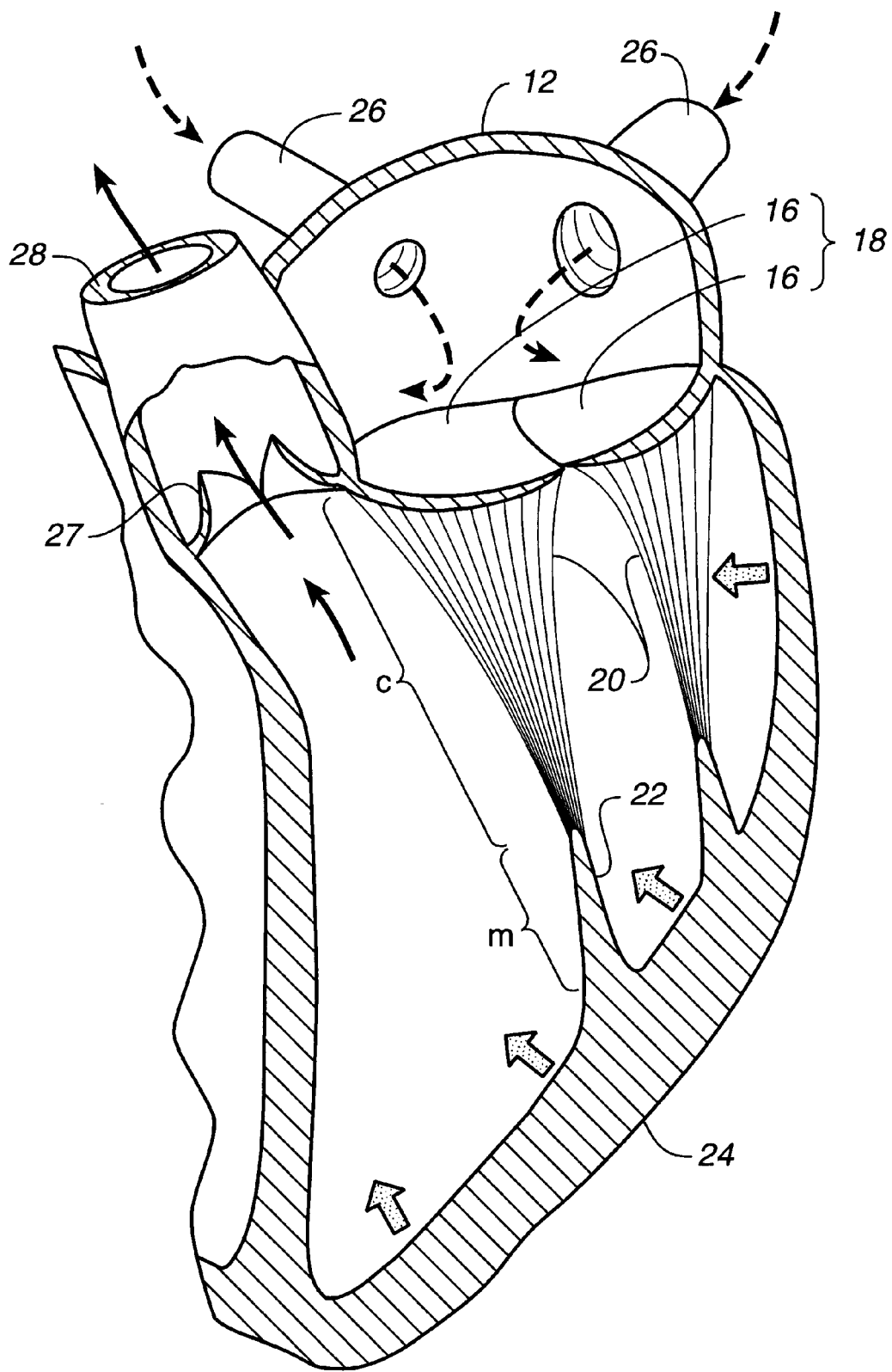
FIG._2

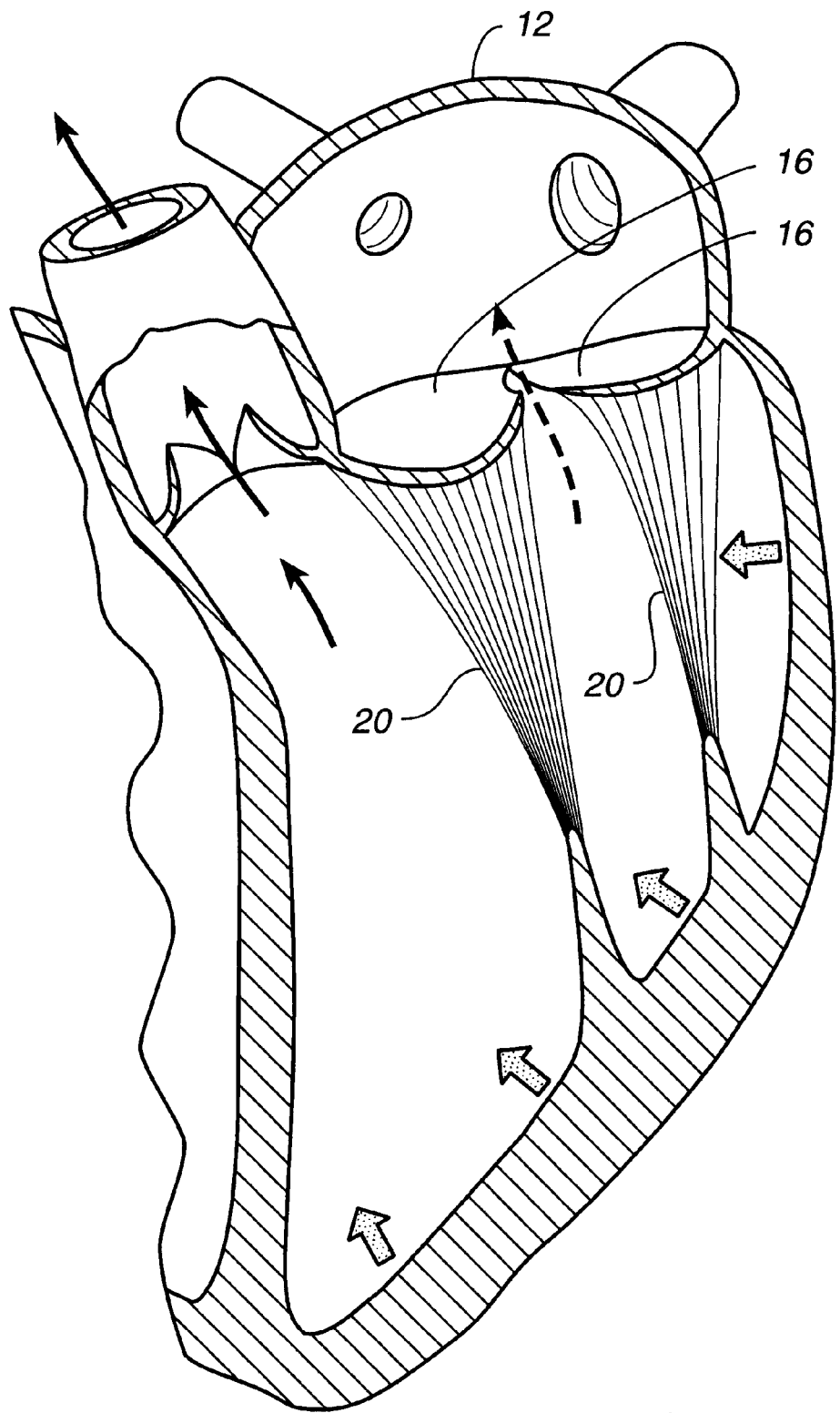
FIG._3

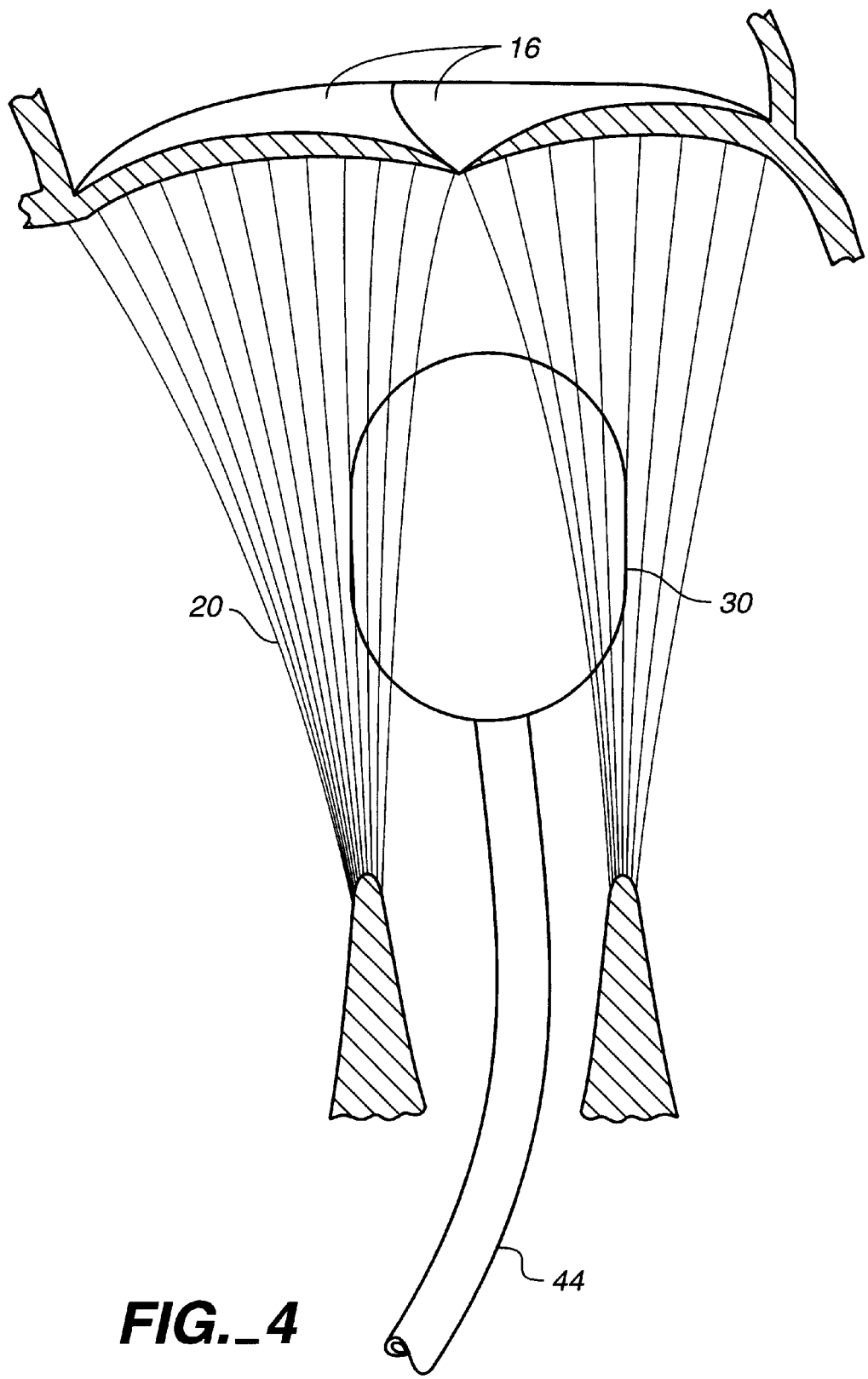
FIG._4

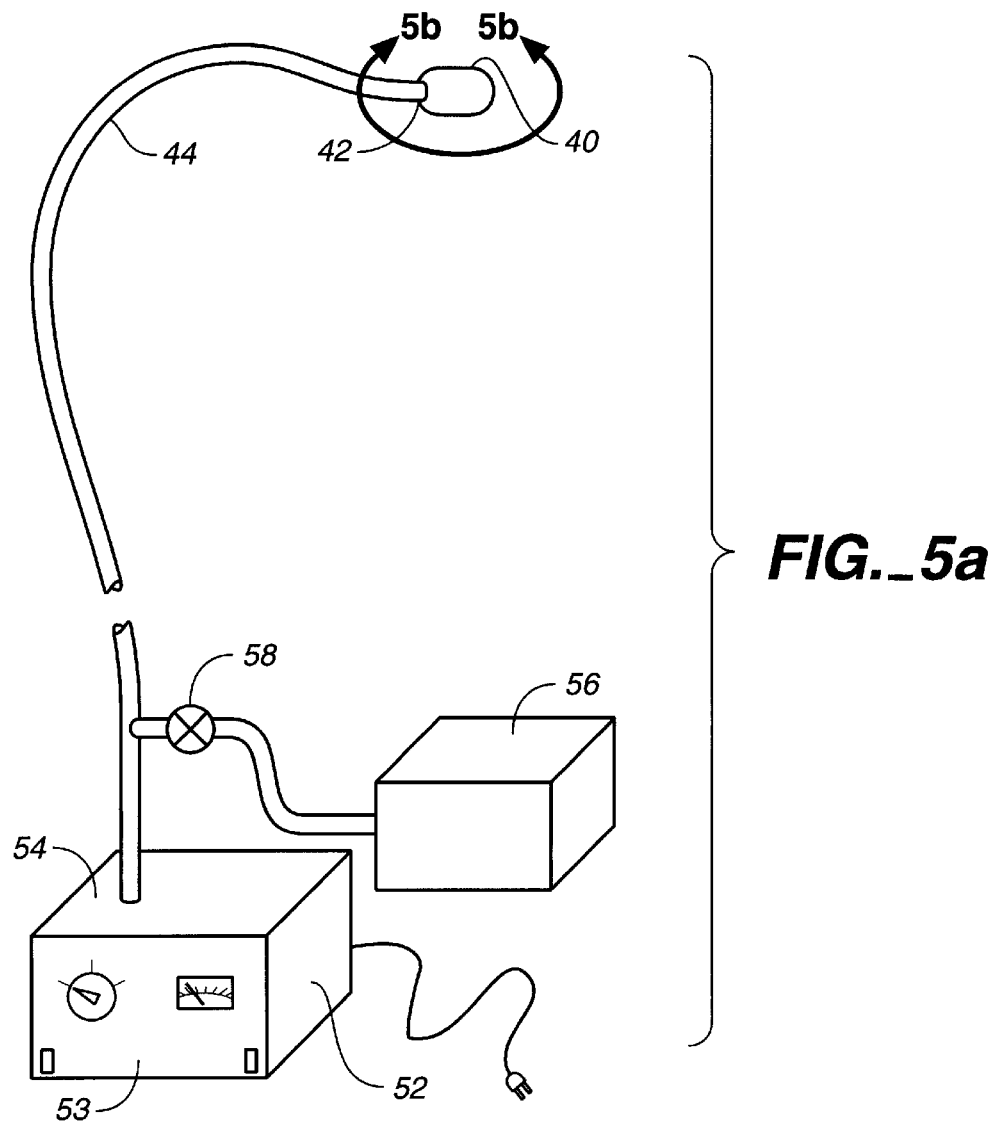
FIG._5a
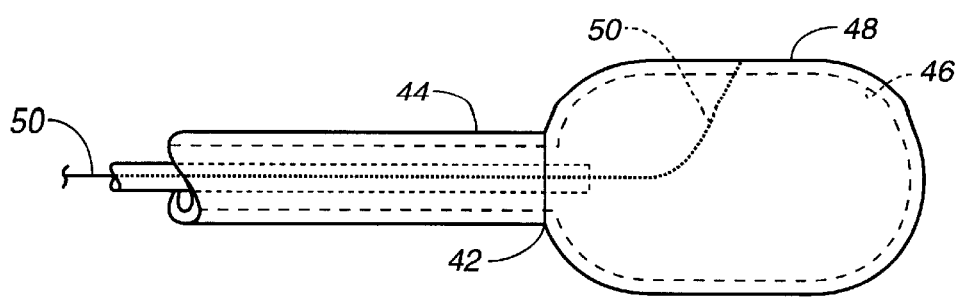
FIG._5b

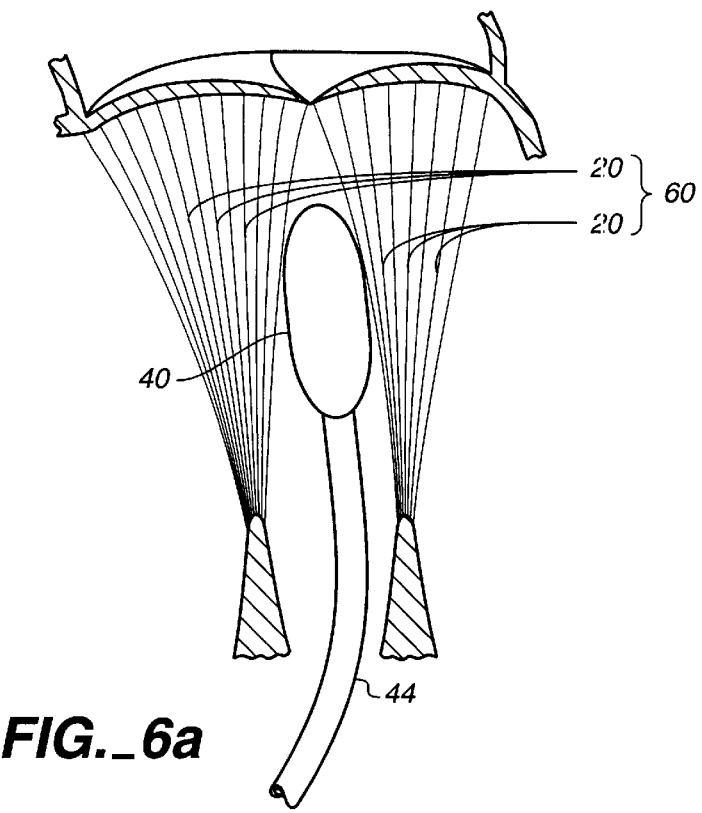
FIG._6a
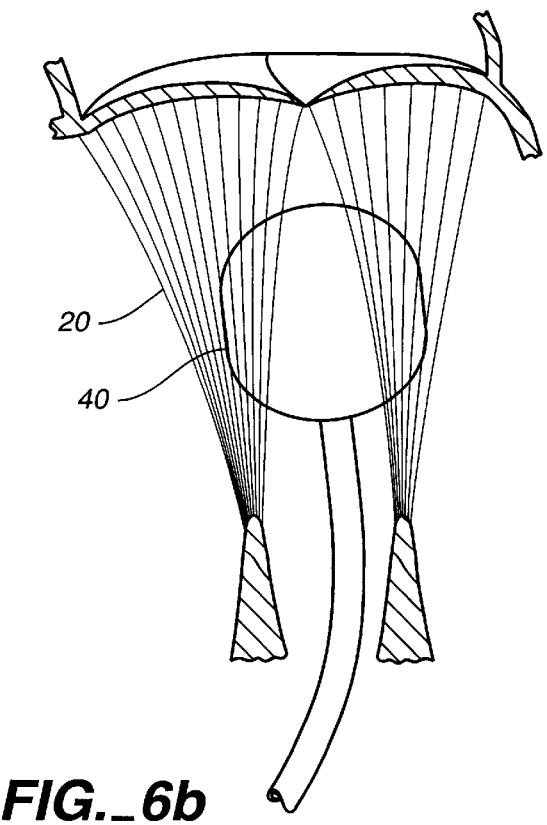
FIG._6b

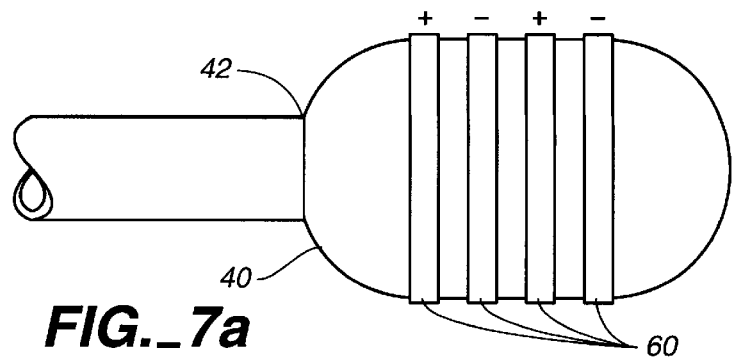
FIG._7a
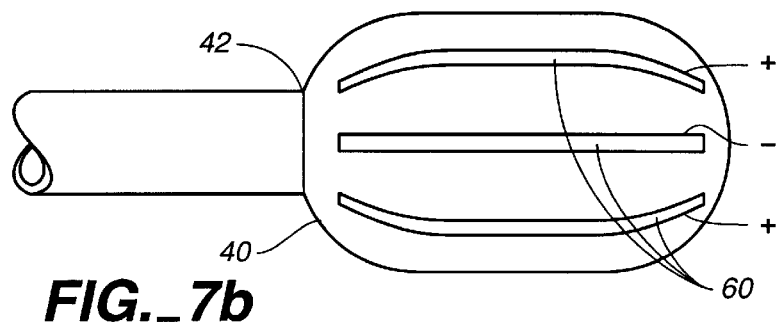
FIG._7b
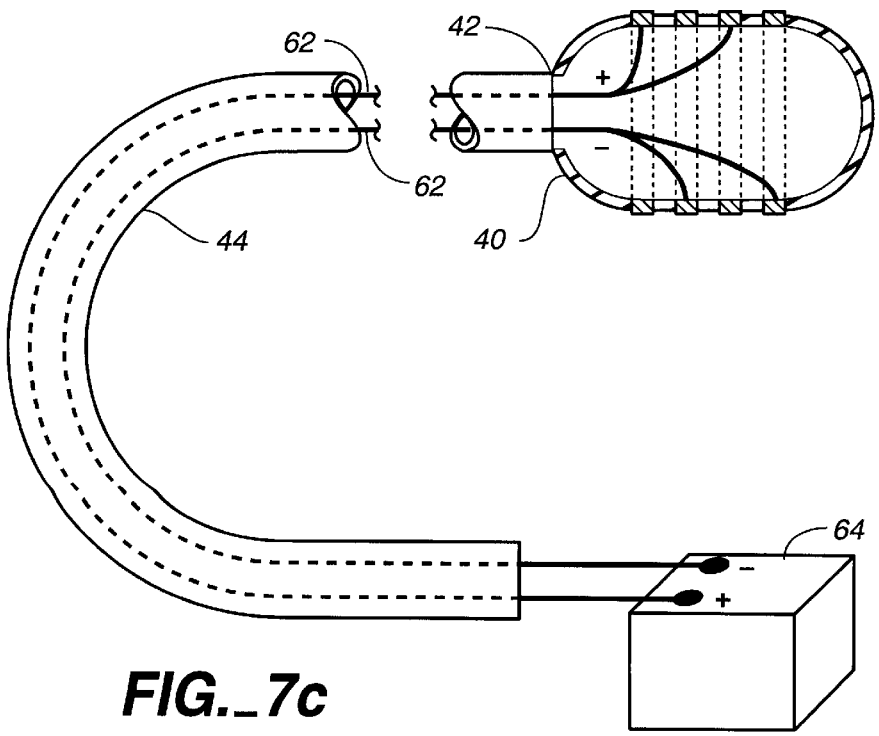
FIG._7c

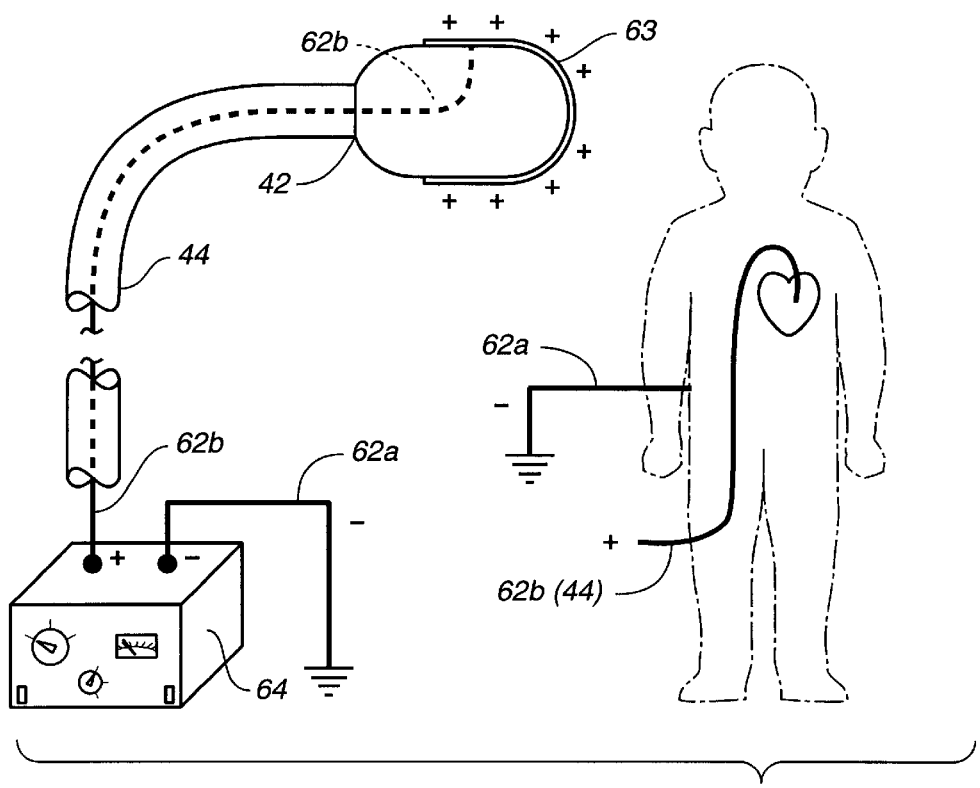
FIG._7d
FIG._8
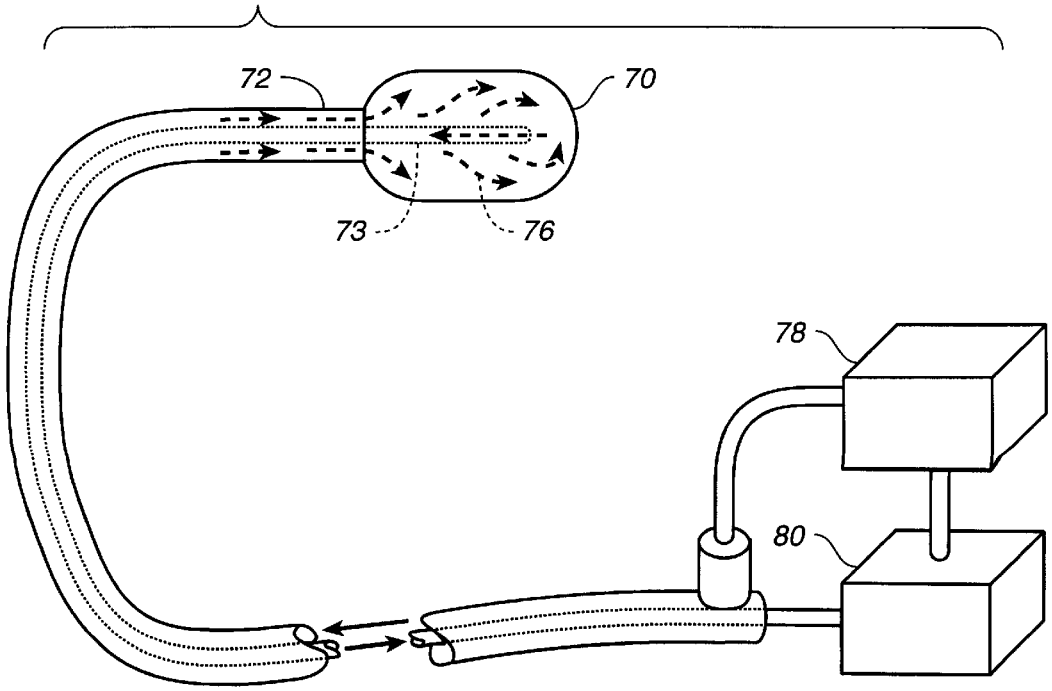

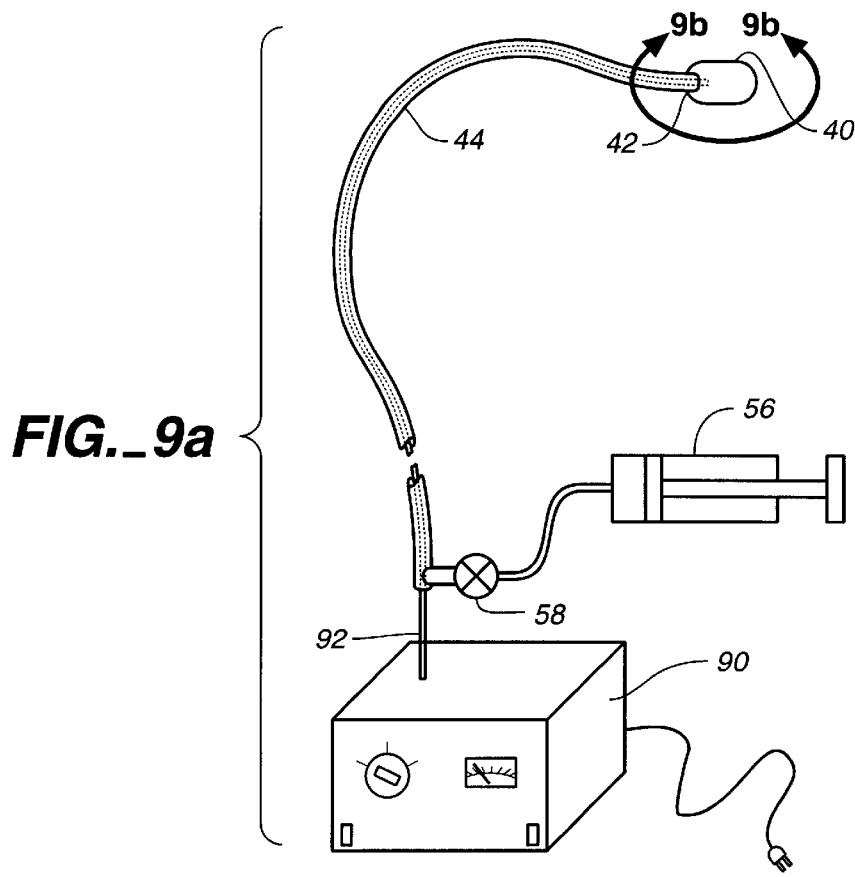
FIG._9a
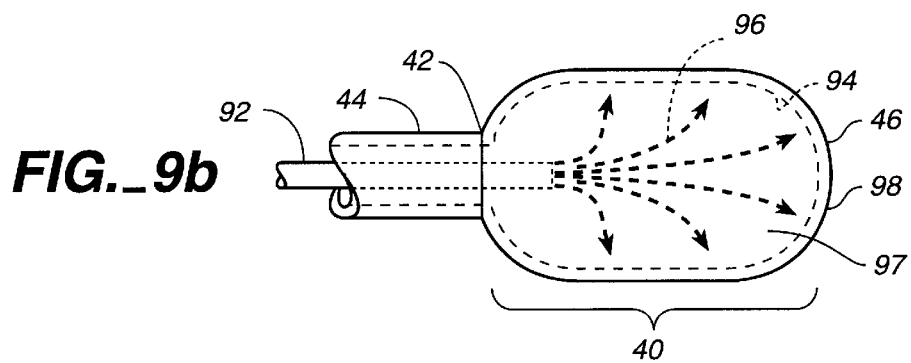
FIG._9b
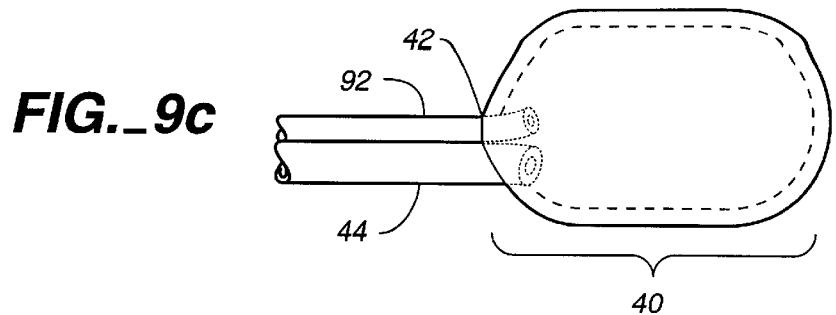
FIG._9c

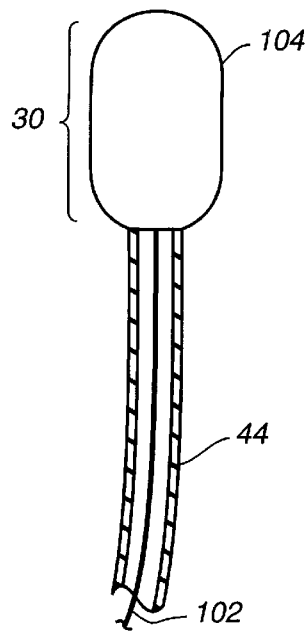
FIG._10
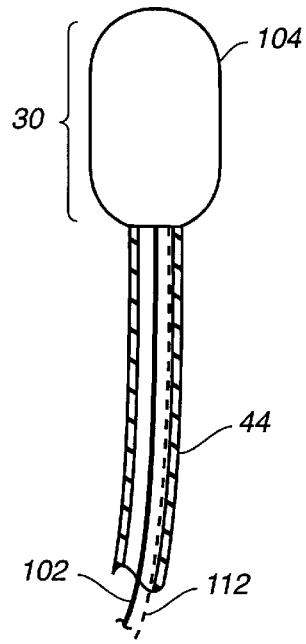
FIG._11a
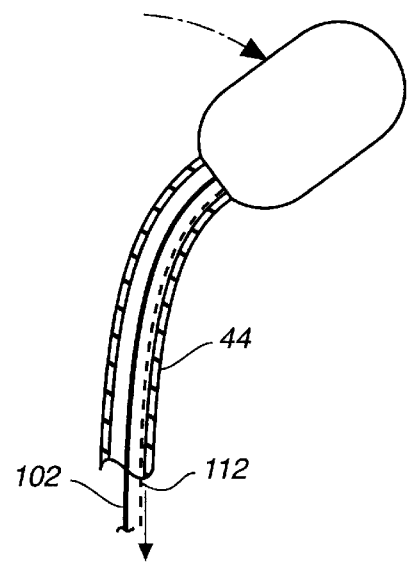
FIG._11b
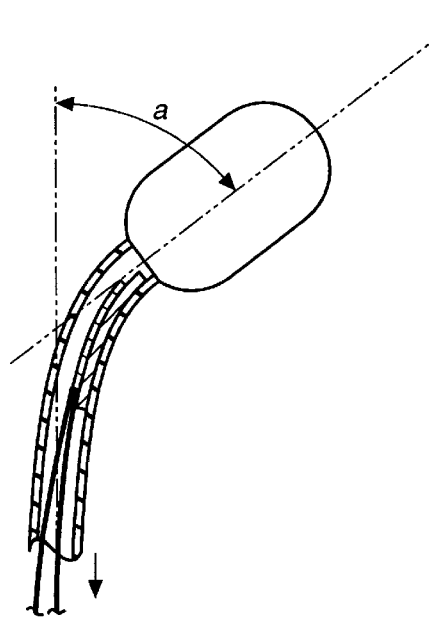
FIG._12a
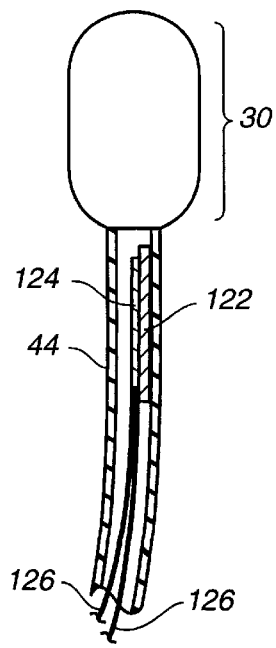
FIG._12b

METHOD AND DEVICE FOR SOFT TISSUE MODIFICATION

FIELD OF THE INVENTION

The present invention relates to a device and method of using the device to change the length of the chordae tendineae of an atrioventricular valve, especially the mitral valve of a human heart.

BACKGROUND OF THE INVENTION

The human heart is a pump comprising four chambers. The two smaller chambers, the left and right atria, are in the upper part of the heart and the two larger chambers, the left and right ventricles, are in the lower part. The heart pumps by the contractions of the strong muscles which make up the outer walls of the four chambers. During normal operation blood returning from the body is collected in the right atrium. When the right atrium becomes substantially full of blood, it contracts forcing blood through the tricuspid valve into the right ventricle. Contractions of the right ventricle send blood in pulses through the large pulmonary artery and into each lung where the blood becomes oxygenated before it returns through the pulmonary veins to fill the left atrium of the heart. Upon filling with blood, the left atrium contracts, squeezing blood through the mitral valve to the left ventricle. In the final step of the operational cycle of the heart, the powerful muscles of the left ventricle contract forcing oxygen-rich blood through the aorta, then into the smaller arteries to eventually deliver blood to tissue throughout the body. The left and right atria and left and right ventricles contract together, so that the heart functions essentially like two ganged two stage pumps.

Improper operation of the valves or failure of the valves to seal properly can significantly affect the efficiency of most pumps and the heart is no exception. Failure of the valves of the heart to function properly can lead to serious health problems or death. Fortunately, medical science has developed techniques to correct certain heart valve problems in some patients, but finding appropriate remedies for heart valve imperfections and failures while minimizing trauma to the patient is still a major challenge for cardiologists and cardiac surgeons.

Each atrioventricular valve is comprised of a number of cusps, many chordae tendineae which act as guy wires or like shrouds of a parachute to stabilize and keep the cusps in postion when closed, and papillary muscles to which the chordae are anchored. If the chordae tendineae are weak or stretched, the cusps which they stabilize may not seal when closed or may even pop backward into the atrium when the ventricle contracts, a condition known as prolapse.

The chordae tendineae may be divided into three groups or "orders". The first group extending from near the apices of the papillary muscles to near the edges of the valve which they stabilize. The tendinous cords subdivide into thinner strands as they near the valve edge. The chordae of the first order insert into the extreme edge of the valve by a large number of very fine strands. Their function seems to be merely to prevent eversion of the opposing borders of the cusps.

The chordae of the second order insert on the ventricular surface of the cusps approximately at the level of the noduli Albini or even higher. These are stronger and less numerous that those of the first order. These function as the mainstays of the valve and are comparable to the stays of an umbrella.

The chordae of the third order originate from the ventricular wall much nearer the origin of the cusps and often form bands or foldlike structures which may contain muscle. Occasionally, particularly on the left side, the chordae of the first two orders, even in normal hearts, may be wholly muscular, so that the papillary muscle seems to insert directly into the cusp. This is not surprising because the papillary muscle, the chordae tendineae, and major parts of the cusps are derived from the embryonic ventricular myocardium and therefore, were all muscular at one time (see Van Mierop, L. H. S. "Anatomy of the Heart," page 67, *Clinical Symposia*, Ciba-Geigy, Summit, N.J. (1965)).

Collagen-containing connective tissue is ubiquitous in the human body and demonstrates several unique characteristics not found in other tissue. It provides the cohesiveness of the musculoskeletal system, the structural integrity of the viscera as well as the elasticity of integument. Intermolecular cross links provide collagen connective tissue with unique physical properties of high tensile strength and substantial elasticity. Collagen fibers shrink and tighten when elevated in temperature. This unique molecular response to temperature elevation is the result of rupture of the collagen stabilizing cross links and immediate contraction of the collagen fibers to about one-third of their original linear dimension. Additionally, the caliber of the individual fibers increases greatly, over four fold, without changing the structural integrity of the connective tissue.

One technique for altering collagen connective tissue involves heating the tissue by means of infrared laser energy. Another technique involves inducing heat in the tissue by exposure to radio frequency (rf) or microwave radiation. It is also possible to heat the collagen tissue directly by contact with a warm probe or catheter heated with electricity or by circulation of a heated fluid. The use of infrared laser energy as a corneal collagen shrinking tool of the eye has been described and relates to laser keratoplasty (see U.S. Pat. No. 4,976,709). The importance of controlling the delivery of the energy, that is controlling the localization, time, and intensity, of the energy is critical to provide the soft tissue shrinkage effects without excess collateral damage. Another technique for altering collagen is taught in U.S. Pat. No. 5,458,596 to treat joints.

There is a need to remodel, e.g., strengthen, tighten, and shorten, tissue of the heart to correct faults and increase cardiac efficiency in certain patients. In particular, the chordae tendineae can be tightened to prevent valve prolapse. The art teaches that such remodeling in some cases can be achieved by surgical manipulation, usually requiring open heart surgery, a major, complicated operation. A less invasive remodeling procedure is needed which would lower the risk to the patient.

Copending U.S. patent application Ser. No. 08/739,820, filed Oct. 30, 1996, now U.S. Pat. No. 5,827,268 teaches heating heart tissue with a heat producing catheter as a treatment for Patent Ductus Arteriosus. Further, copending U.S. patent application Ser. No. 08/768,607, filed Dec. 18, 1996 discloses a device and treatment by heating collagen tissue of the heart to repair damage from a myocardial infarction.

It is an object of the present invention to provide a technique for improving atrioventricular valve performance and preventing prolapse by remodeling the corresponding chordae tendineae with heat. It is also an object to provide devices for this remodeling technique as well as methods of teaching the technique.

SUMMARY OF THE INVENTION

The present invention provides a means and method of improving performance of a human heart wherein the chordae tendineae of an atrioventricular valve are stretched or weak allowing leakage or prolapse of the valve. In particular, the invention is directed to a device and method for applying heat, directly or indirectly, to shorten and make firm the chordae tendineae of an atrioventricular valve, in particular, of the mitral valve, to prevent prolapse.

One aspect of the invention provides for a device for insertion into a ventricle of a human heart and for positioning it in contact with, or in close proximity to, the chordae tendineae of an atrioventricular valve, e.g., the mitral valve. The device is capable of applying a controllable amount of heat directly to, or inducing heat in, the chordae tendineae to cause shortening and firming thereof.

In one embodiment the device comprises a catheter having a heat producing, i.e., direct heating or heat inducing, means at the end which is positioned in contact with, or in close proximity to the chordae tendineae. The direct heating means include electrical resistance heating elements, a balloon which is heated by internal absorption of light or infrared rays, and and a tube through which is circulated a heated fluid. The heat inducing means include radiators of radio frequency (rf), microwave, infrared radiation, and coherent and noncoherent light.

A second aspect provides for a method for treating atrioventricular valve leakage or prolapse comprising the steps of:

a) Inserting a heating device into the ventricle associated with the atrioventricular valve to be treated entering the patient's heart through the chest wall or transvascularly, b) Maneuvering the heating device into contact or close proximity with chordae tendineae of the atrioventricular valve to be treated, c) Causing the heating device to heat the tissue of the chordae tendineae and continue the heating until the chordae tendineae have been shortened and firmed to the desired degree.

d) Removing the device from the patent's heart and closing incisions necessitated during the insertion in step a.

Those acquainted with medical procedures, as well as laymen, will appreciate that any medical procedure involving entry into the heart, such as the method taught herein, should be practiced only by a medical professional with extensive training and experience in cardiology and cardiac surgery. Therefore, yet another aspect provides a method for training a person, e.g., a surgeon learning cardiac procedures, to perform the method for treating atrioventricular valve leakage or prolapse of the above second aspect. The training method includes the steps of demonstrating and instructing how to do steps a through d and the closely supervising the person receiving the training in executing steps a through d until that person has mastered these steps.

BRIEF DESCRIPTION OF THE DRAWINGS

As used herein, like reference numbers will designate similar elements in various embodiments of the present invention. In some cases the figures are not to scale, and some components have been emphasized to better illustrate the present invention:

FIG. 1 is a schematic cross sectional view of the left side of a human heart in diastole showing the components thereof needed to describe the present invention. (For simplicity and ease of viewing, the right side and other components are not illustrated.)

FIG. 2 is a schematic cross sectional view, similar to FIG. 1, but with the heart in systole.

FIG. 3 is a schematic cross sectional view of the left side of a human heart in systole illustrating the abnormality of prolapse.

FIG. 4 is a schematic illustration of the placement of a device of the present invention among the chordae tendineae.

FIG. 5a is a schematic view of the first embodiment of the device of the present invention.

FIG. 5b is an enlarged view of the circled portion of FIG. 5a.

FIG. 6a is a schematic view of the first embodiment placed among the chordae tendineae before inflation.

FIG. 6b is an enlarged view similar to FIG. 6a, but after inflation.

FIGS. 7a, 7b, 7c, and 7d are schematic views of the second embodiment of the device of the present invention.

FIG. 8 is a schematic view of the third embodiment of the device of the present invention.

FIG. 9a is a schematic view of the forth embodiment of the device of the present invention.

FIG. 9b is an enlarged, schematic view of the circled portion of FIG. 9a showing a cross section of the balloon tip.

FIG. 9c is an enlarged, schematic view of the circled portion of FIG. 9a for an alternative form of the forth embodiment showing a cross section of the balloon tip.

FIG. 10 is a general schematic view of the device of the fifth and sixth embodiments.

FIG. 11a and FIG. 11b are schematic views of the fifth embodiment.

FIG. 12a and FIG. 12b are schematic views of the sixth embodiment.

DETAILED DESCRIPTION OF THE INVENTION

Many types of tissue can be molded and remodeled to correct defects and dysfunction. One means is by physical manipulation using mechanical instruments and/or balloons (such as those used in percutaneous transluminal angioplasty) to effect selective shrinking, stretching, flattening, thinning or thickening in addition to changing the material properties of the tissue. These changes of properties include alteration of the elastic coefficient of the tissue causing it to be stiffer, changing the tensile strength of the tissue, changing the shear strength of the tissue, and changing the floppiness or resiliency of the tissue. When the tissue is close to the surface of the skin or part of a non critical organ, physical manipulation is feasible and can be executed with minimal trauma to the patient. However, when the tissue is in an internal organ, in particular, in the heart or other vital organ, molding and remodeling by physical manipulation can involve complicated and often risky surgery and bypass/stopping of the heart.

Molding or remodeling or sterilizing of certain soft tissue, e.g., collagen, can also be carried out using heat. The heat can be applied to, or induced in, the tissue by a number of methods including:

1) directly, i.e., conductively, heating by contact with a heating medium such as a heating element or placing a heated fluid, either liquid or gas, in contact with the surface of the tissue;

2) radiantly heating by placing a source of infrared radiation in close proximity to the tissue; and 3) inductively heating by directing electromagnetic energy, such as radio frequency, microwave, or light from either coherent or incoherent sources, into the tissue. An electric current may also be passed through the tissue by means of electrodes inserted into, or placed on the surface of, the tissue.

Where molding and remodeling of tissue with heat is possible, extensive surgery and the accompanying trauma may be avoided. For example, an incision only large enough to allow insertion of a thin catheter may be adequate to place a heating device at the site to be molded or remodeled. Further, where the tissue is in the interior of the heart, open heart surgery might be avoided by manipulating a catheter through a blood vessel, into the heart and into the area of the tissue to be remodeled.

When the chordae tendineae of an atrioventricular valve are stretched or become weak, they may not be able to hold the valve firmly closed against the systolic blood pressure, resulting in back flow of blood into the atrium or even prolapse of the valve. It is possible to surgically shorten, and thus tighten, the chordae tendineae. This is by no means a simple procedure because it involves open heart surgery. However, the chordae tendineae tissue is substantially composed of collagen. Collagen tissue shrinks when heated as a result of the restructuring of collagen and other protein and/or the change in hydration of the tissue. Therefore, in theory, applying heat to, or inducing heat in, the chordae tendineae can shorten and remodel the chordae tendineae to the point that they properly stabilize their associated atrioventricular valve. However, in practice, shortening and remodeling the chordae tendineae requires a precise, stable, and accurately controllable source of heat in connection with a means to maneuver the heat source with precision to the site of treatment. Further, sensitive and precise means of monitoring the degree of shortening and remodeling is required by the operating surgeon.

Although both of the atrioventricular valves, i.e., the tricuspid and the mitral, are subject to leakage and prolapse because of stretched chordae tendineae, most often the difficulty is seen with the mitral valve. Therefore, to simplify the following discussion and explanation, the mitral valve and its associated chordae tendineae will be used as the example. However, it is to be understood that what is said about the mitral valve chordae tendineae also applies to the tricuspid valve chordae tendineae.

Referring to FIG. 1, the left side of a human heart 10 comprises two of the four major chambers of the heart, the left atrium 12 and the left ventricle 14. The mitral valve 18 is comprised of cusps 16, which are stabilized by multiple chordae tendineae 20 which are connected to the papillary muscles 22 at one end and to the cusp 16 at the other. The papillary muscles 22 are attached to the inner portion of the muscular 24 wall of the left ventricle 14.

For ease of illustration and clarity only the left side of the heart has been depicted in FIG. 1 and related drawings. However, it will be appreciated by those skilled in the medical arts that the components of the right side of heart and the functions of those components are substantially similar to those shown in the figures and described below. Thus, the method and devices taught herein are applicable to both side of the heart.

FIG. 1 shows the left side of the heart 10 in diastole. That is the mitral valve 18 is open and the chordae tendineae 20 are in a relaxed state. Oxygenated blood (indicated by the dashed-line arrows) is returned to the heart from the lungs through the pulmonary veins 26 and is collected in the left atrium 12. As indicated by the heavy arrows, the muscles in the walls of the atrium 12 are starting to contract, thereby forcing the oxygenated blood into the left ventricle 14 via the mitral valve 18. At the stage depicted in FIG. 1, the cusps 16 of the mitral valve 18 extend into the left ventricle 14. The aortic valve 27 is closed.

Referring to FIG. 2, as the heart enters systole the muscles 24 in the wall of the left ventricle 14 contract (indicated by the heavy arrows), forcing blood (indicated by light arrows) out through the aortic valve 27 and out through the aorta 28. The increased pressure against the ventricle side of the cusps 16 forces them toward the left atrium 12 until they seal together, i.e., the mitral valve 18 closes, stopping the flow of blood from the left ventricle 14 back into the left atrium 12. Note that when the ventricle contracts, the distance from ventricular wall to cusp shortens, so the papillary muscle must contract in order for the valve to stay in closed, i.e., the length to the cusp plus the length of the papillary muscle, c+m in FIG. 2, must decrease.

In a normal heart, the chordae tendineae 20 are now under tension and prevent the cusps from being forced back into the atrium 12 by the systolic pressure within the left ventricle 14. While the muscles 24 of the left ventricle 14 are forcing blood out through the aorta, the left atrium 12 with its wall muscles in a relaxed state is filling with blood (indicated by the dashed-line arrows) returning from the lungs through the pulmonary veins 26. When the muscles 24 have finished contracting, i.e., systole is substantially complete, and they start to relax, the muscle in the walls of the left atrium 12, contract forcing the cusps 16 into the left ventricle 14, thus opening the mitral valve 18. The blood then flows from the left atrium 12 and fills the left ventricle 14 returning the heart to diastole depicted in FIG. 1.

Referring to FIG. 3, where the chordae tendineae 20 are stretched, an abnormal condition, the cusps 16 are not sufficiently stabilized to prevent being forced back into the left atrium 12 by the intraventricular blood pressure differential during systole. Therefore, some blood flows back into the left atrium 12 (indicated by the doted-line arrow) and consequently the left atrial pressure is increased, resulting in lung damage and less blood is pumped to the body during each operational cycle of the heart.

Referring to FIG. 4, a heating device 30 at the end of a catheter shaft 44 is inserted into the left ventricle 14 (not shown, but implied in FIG. 4; see FIG. 1–3) and placed in contact with, or in close proximity to, the chordae tendineae 20. Typically, a guide wire lumen which provides for insertion over a wire such that the device can be place into the heart and located adjacent to the chordae tendineae is employed. The operating surgeon may use echocardiography, fluoroscopy or other techniques of the art to visualize the movement of the device 30 while maneuvering it through the left ventricle 14 and among the chordae tendineae 20.

Techniques for negotiating a catheter through a human body, into the body's heart, and manipulation of the catheter within the heart to perform a medical procedure are well know in the art of medicine, and in particular, the arts of cardiac surgery and interventional cardiology.

FIG. 5a shows one specific embodiment of the device of the present invention which is a balloon 40 placed at the distal end 42 of a catheter shaft 44, i.e. an inflation lumen. As shown in FIG. 5b, an enlarged, cut away view of the device, the balloon 40 is constructed of an elastomeric material 46 having a metallic exterior coating 48. Catheter shafts suitable for use in the present invention are substantially any of the catheter shafts in current clinical use for cardiac procedures. Balloons suitable for the present invention may be of similar material and design as those currently being used in percutaneous transluminal angioplasty. For a review of the state of the art, see U.S. Pat. Nos. 4,807,620; 5,057,106; 5,190,517; 5,281,218; 5,314,466; 5,370,677; 5,370,678; 5,405,346; 5,431,649; 5,437,664; 5,447,529; and 5,454,809 all incorporated herein by reference.

Referring to both FIG. 5a and FIG. 5b, the metallic coating 48 is connected via a cable 50, e.g., a coaxial cable, through the wall of the balloon 40, and through the catheter shaft 44 to a radio frequency (rf) generator 52 at the proximal end 54 of the catheter shaft 44. The rf generator 52 may be placed in any location outside the body of the patient, but would preferably be located so that the controls 53 are within convenient reach of the operating surgeon. For example, the frequency (rf) generator 52 might be in a shielded location, remote from the other instruments in the operating room, but the controls 53 might be in a module which could be held in the surgeon's hand. The catheter shaft 44 is also connected to a syringe 56 or other similar device for forcing a fluid such as a gas, e.g. air, or a liquid through valve 58 to allow the balloon to be inflated with the fluid as the operating surgeon deems appropriate.

The frequency range of rf radiation useful in the present invention is typically about 10 MHZ to about 1,000 MHZ, preferably in the range of about 50 MHZ to about 100 MHZ. However, frequencies outside this range may be used at the discretion of the operating surgeon.

Alternatively, microwave radiation typically in the frequency range of about 1,000 MHZ to about 2,000 MHZ, preferably in the range of about 1,100 MHZ to about 1,500 MHZ, may be used in place of rf radiation. However, as above, frequencies outside this range may be used at the discretion of the operating surgeon. The rf generator 52 is replaced with a microwave generator, and the cable 50 is replaced with a waveguide. Other modifications familiar to those skilled in the art may also be required.

Referring to FIG. 6a and FIG. 6b, when the operating surgeon has placed the collapsed balloon within the pyramid 60 formed by the chordae tendineae 20 as schematically depicted in FIG. 6a, the balloon is inflated through the catheter shaft 44 with fluid from a syringe 56 (see FIG. 5a) located conveniently for the surgeon. The balloon is inflated until it is forcing the chordae tendineae 20 apart and the metallic coating of the balloon is substantially in contact with the surface of the chordae tendineae 20 as depicted in FIG. 6b.

Preferably, the exact amount of inflation is determined by the operating surgeon who monitors the balloon expansion by means of fluoroscopy, echocardiography, or other suitable imaging methods of the art; and who considers such factors as the condition and age of the patient and the degree of stretch in the chordae tendineae 20, which is to be removed. As the balloon 40 expands, chordae tendineae 20 are forced outward, effectively shortening them, the amount of shortening can be determined and locked in by this method. The balloon 40 can be deflated or inflated as often as the operating surgeon deems necessary. Generally, the heat required is induced in the tissue of the chordae tendineae 20 by the rf or microwave radiation emitting from the balloon tip. The rf or microwave energy would be applied while observing for changes via simultaneous echocardiography, fluoroscopy, or other suitable imaging methods of the art.

FIG. 7a, FIG. 7b, FIG. 7c, and FIG. 7d illustrate the second embodiment of the device of the present invention which is similar to the embodiment shown in FIG. 5, and described above. That is, the device is comprised of a balloon 40 placed at the distal end 42 of a catheter shaft 44. except that rather than having a continuous metallic coating (as in FIG. 5), the balloon has strips 60 of metallic coating alternating with strips without coating. The strips 60 may run latitudinally as shown in FIG. 7a or longitudinally as shown in FIG. 7b on the surface of the balloon 40, and act as electrodes to transmit electric energy into the tissue of the chordae tendineae 20.

Referring to FIG. 7c, the strips 60 are alternatingly positively or negatively changed by insulated cables 62 running through the wall of the balloon and through the catheter shaft 44 to a source of direct electric current 64 having its controls located conveniently for the operating surgeon. Those skilled in the art will appreciate that the device of this embodiment may also be used with controllable alternating electric current with little or no modification.

Alternatively, in the monopolar mode as shown in FIG. 7d, a lead 62a from one of the poles of the source of electric current 64 is connected to the patient's body which serves as a ground. A lead from the other pole of the source of electric current 62b is passed through the catheter shaft 44 (in FIG. 7d this is noted as "62b(44)") and connects with the metallic strips on the exterior of the balloon 40 through a lead passing through the wall of balloon 40. (See U.S. Pat. No. 4,765,331 incorporated herein by reference.) In this alternative case, the balloon may have a continuous metallic coating 63 similar to that shown for the balloon 40 in FIG. 5b. Further, conductive material may be on the inside of a balloon fabricated of a conductive (non-insulating) material. For simplicity of illustration, FIG. 7d shows the ground as negative, but it could just as well be positive. (See U.S. Pat. Nos. 5,230,349 and 5,462,545 incorporated herein by reference.)

The employment of the embodiment shown in FIG. 7a, FIG. 7b, FIG. 7c, and FIG. 7d as described above is substantially the same as the embodiment shown in FIG. 5a and FIG. 5b. The power and duration of application are at the discretion of the operating surgeon. However, in general, the power used in this embodiment of the device ranges from about 0.1 to about 10 watts for about 1 second to about 360 seconds and preferably about 1 to about 5 watts for about 3 to about 30 seconds.

FIG. 8 shows the third embodiment of the device of the present invention wherein the heat generated by the balloon is not supplied by rf or microwave radiation or an electric current, but a circulating, hot fluid. Referring to FIG. 8, a balloon 40 (substantially the same as balloon 40 of the first embodiment, but a metallic coating is not required in this embodiment) is attached to a catheter 72 containing a smaller, coaxial catheter 73. (Catheter 72 may be substantially the same as catheter 44 of previous embodiments. Coaxial catheter 73 is substantially the same as catheter 72 differing only in size.)

A heated fluid 76, which may be a liquid, such as water or physiologically compatibly saline solution, is pumped by a metering, circulating pump 78, through a heating unit 80, then through the outer, catheter 72 to the balloon 40. The heated fluid in turn heats the surface of the balloon 40 then leaves through the inner, coaxial catheter 73 to return to the pump. A positive pressure is maintained within the system to keep the balloon at the proper inflation. This embodiment is employed is in substantially the same manner as the other embodiments described above regarding its use to heat the chordea tendieae. The choice of the temperature of the circulating liquid is at the discretion of the operating surgeon, but will usually be in the range of about 60° C. to about 95° C.

The fourth embodiment illustrated in FIG. 9a, FIG. 9b, and FIG. 9c is similar in configuration to the first embodiment shown in FIG. 5a and FIG. 5b and described above except it uses coherent or noncoherent light or infrared radiation as the source of heat. As with the embodiment shown in FIG. 5a and FIG. 5b, a balloon at the distal end of a catheter shaft 44 (inflation lumen) is inflated to come in contact with, or close proximity to, the chordae tendineae as shown in FIG. 6b to enable the operating surgeon to apply heat to the chordae tendineae.

Referring now to FIG. 9a and FIG. 9b; to the output of a light source 90, such as a coherent light source, e.g., a laser, is connected a light pipe 92, e.g., an optical fiber bundle. The light pipe 92 runs within the catheter shaft 44 to just inside the balloon 40 at the distal end of the catheter shaft 44. Referring to FIG. 9c, alternatively, the balloon is attached to the distal end 42 of the light pipe 92 and the catheter shaft 44 is fastened to the side of the light pipe 92. The catheter shaft 44 penetrates the balloon 40 so that the inflating fluid can be forced through the catheter shaft 44 into the balloon 40. The balloon 40, fabricated from an elastomeric material 46, is inflated by forcing a fluid through the catheter by means of a syringe 56 and associated valve 58 in a similar manner as show in FIG. 5a and described above for the previous embodiments.

The interior surface 94 of the balloon 40 is coated with a light absorbing material which converts a substantial amount of the light rays 96 striking the interior surface 94 into heat. The light absorbing coating is chosen from coatings known in the art to maximize the conversion of light to heat for the particular wave length of light being used. For example, a simple, flat black coating could be used for longer wavelength light. The heat generated as the light is absorbed by the interior surface 94 is transferred directly to the outer surface 98 of the balloon 40 or to the fluid 97 inflating the balloon 40. In turn, heat is transferred to the chordae tendineae primarily by conduction, but to some extent by convention and radiation, from the outer surface 98.

Alternatively, the chordae tendineae may be heated directly by light with a light pipe in contact with the chordae tendineae. Suitable light may be supplied by a garnet or ir laser.

Where infrared radiation is used rather than visible light, the light source 90 shown in FIG. 9 is replaced with a source of infrared radiation and the light absorbing material is replaced with an infrared absorbing material. Other modifications familiar to those skilled in the art may also be required.

The above four embodiments rely on a balloon which is inflated in the vicinity of the chordae tendineae to bring the source of heat at the end of the catheter in contact or close proximity to the chordae. It is also possible to mechanically manipulate the heat producing tip of the catheter to contact the surface of the chordae tendineae. In particular, the portion of the catheter adjacent to the heat producing tip can be caused to bend or to curl up by mechanical or electro-mechanical means.

Referring to FIG. 10, a heat producing tip 30 is attached to the distal end of a catheter shaft 44 and a supply conduit 102 supplies energy to produce heat in the heat producing tip 30. Unlike the heat producing balloon tip in the four previous embodiment which is expanded to contact the tissue to be heated, the heat producing tip 30 has fixed dimensions. Preferably the diameter of the heat producing tip 30 is equal to, or slightly larger than that of the catheter shaft 44 and has a substantially round end 104 to facilitate passage of the catheter shaft 44 through blood vessels and into a ventricle of the heart.

The heat producing tip 30 may generates heat by means described for the previous four embodiments. That is, the heat producing tip 30 may be equipped with an rf, infrared, or microwave emitting means to induce heat in tissue in its close proximity. Alternatively, it may be heated internally by a flow of heated fluid, an electrical heating element, internally absorbed coherent and noncoherent light, and internally absorbed infrared radiation. In turn, the heat producing tip 30 heats tissue which it contacts by conduction or tissue which is in its close proximity by convection. Alternatively, the light can be shined directly on the chordae tendineae to heat them.

The fifth embodiment of the device of the present invention is illustrated in FIG. 11a and FIG. 11b. Referring to FIG. 11a, the heat producing catheter shown in FIG. 10 and described above is equipped with a line 112, such as a polymeric cord (mono or multi-strand) or a metallic wire connected to the heat producing tip 30, extending internally the length of the catheter shaft 44, and exiting the proximal end of the catheter shaft 44. Pulling firmly on the line 112 with respect to the catheter causes the portion of the catheter shaft 44 adjacent to the heat producing tip 30 to bend as illustrated in FIG. 11b. In practice, the line 112 is pulled while holding the catheter shaft 44 substantially steady. The amount of bend is controlled by the judicial manipulation of the line 112 by the operating surgeon who may use echocardiograph, fluoroscopy or other techniques of the art to visualize the movement of the heat producing tip 30 and place it in contact with the tissue of the chordae tendineae.

The sixth embodiment of the device of the present invention is illustrated in FIG. 12a and FIG. 12b. Referring to FIG. 12a, the heat producing catheter shown in FIG. 10 and described above is equipped with a stiff strip of material 122 which deflects when heated. The stiff strip of material 122 is located longitudinally on, and fasten to, the inner wall of the catheter shaft 44. The length of the stiff strip of material 122 varies according to the particular application, but typically is be from about 5 mm to about 75 mm and its width is about 0.05 to about 0.25 times the inner circumference of the catheter 44. This strip may also have a semicircular cross section to conform to the inner wall of the catheter 44. This strip will typically have one end in close proximity to the heat producing tip 30 but its placement will vary according to the preference of the operating surgeon. It may be desirable to have multiple strips to improve maneuverability of the tip.

In contact with, or close proximity to the stiff strip of material 122 is a means of suppling a controlled amount of heat, such as an electric heating element 124, to the stiff strip of material 122. Suppling energy to activate the means of supplying a controlled amount of heat is a conduit means, such as one or more conductors of electric current 126, e.g., electric wires.

The stiff strip of material 122 may be made of two or more strips of metal with different coefficients of expansion bond together in a way to maximize their contact. Such materials are generally known as "bimetallic strips." Upon heating, bimetallic strips deflect or distort, and can be manufactured in a wide range of heat sensitivities. Bimetallic strips are commonly used in thermostats and in intermittent electrical switches.

Alternatively, shape memory metal may be used in place of a bimetallic in the above embodiment. A shape memory metal is a metal alloy having the property of assuming a predetermined, i.e., programmed, shape upon reaching a predetermined, i.e., activation temperature. Such metals are well know in the art (see for example U.S. Pat. Nos.

4,621,882 and 4,772,112). For the present embodiment a shape memory metal should have the property of assuming a deflection away from the axis of the catheter shaft 44 (shown in FIG. 12a as angle a) when activated, i.e., heated in excess of the normal body temperature of a human.

The amount of deflection and the activation temperature programmed into the memory metal would be chosen according to the particular application. The present embodiment would likely be supplied in a variety of programmed deflections and activation temperatures to allow selection by the operating surgeon to best suit the application. However, a typical amount of deflection angle a in FIG. 12b, chosen is in the range of about 30° to about 120° away from the axis of the catheter shaft 44 and the activation temperature chosen is typically in the range of about 5° C. to about 20° C. above a human's normal body temperature.

Optionally the stiff strip of material 122, is attached to a strip of material which defects upon application of force, but which rapidly returns to its original configuration upon release of the force. For example, a strip of spring steel of similar length to the stiff strip of material 122 and bonded to it would assist the stiff strip of material 122 in quickly returning to its initial shape. Those skilled in the art of cardiac surgery will appreciate that upon completion of shortening of the chordae tendineae by heating, removal of the catheter from the heart would be greatly facilitated if the catheter were in the same configuration as when it was inserted.

The stiff strip of material 122 itself may be used as the heating element if the material is only a moderately conductor to an electric current and no other heating element would be needed. That is, the electrical resistance in the stiff strip of material 122 is adjusted so that it heats when an electric current flows through it. It will also be understood that the stiff strip of material 122, when it is conductive, can serve as one of the leads to a heating element.

What is claimed is:

1. A method for treating atrioventricular valve leakage or prolapse comprising the steps of:
   a) inserting the heating portion of a heating device which includes a balloon into the ventricle associated with the atrioventricular valve to be treated by entering a patient's body and heart through the chest wall or transvascularly,
   b) maneuvering the heating portion of the heating device into contact or close proximity with chordae tendineae of the atrioventricular valve to be treated,
   c) assessing the amount of shrinkage needed by inflating the balloon and monitoring the degree of inflation and the bowing of the chordae tendineae,
   d) causing the heating portion of the heating device to heat the tissue of the chordae tendineae and continue the heating until the chordae tendineae have been shortened and firmed to the desired degree, and
   e) removing the heating device from the patent's heart and body and closing incisions necessitated during the insertion in step a.

2. The method of claim 1 wherein step a) comprises inserting the heating device into said ventricle wherein the heating device comprises:
   (i) a tip system capable of heating the chordae tendineae,
   (ii) a source of energy for providing energy to the tip system to cause heating, and
   (iii) a catheter shaft having the tip system at its distal end, the source of energy at its proximal end, and a means of transmitting energy from the source of energy to the tip system.

3. The method of claim 2 wherein step b) comprises maneuvering the tip system into contact with, or in close proximity to, the tissue to be heated.

4. The method of claim 2 wherein step a) comprises inserting the tip system into the ventricle wherein the tip system comprises:
   (i) a balloon capable of heating by emitting energy in the form of electromagnetic radiation,
   (ii) a means for inflating and maintaining the inflation of the balloon, and
   (iii) a means for supplying energy in the form of electromagnetic radiation to the balloon.

5. The method of claim 4 wherein step d) comprises supplying electromagnetic radiation that is in the radio frequency range to the balloon.

6. The method of claim 4 wherein step d) comprises supplying electromagnetic radiation that is in the microwave range to the balloon.

7. The method of claim 4 wherein step d) comprises supplying the electromagnetic radiation that is in the infrared range to the balloon.

8. The method of claim 2 wherein step a) comprises inserting the tip system into the ventricle wherein the tip system comprises:
   (i) a balloon capable of heating by inducing an electrical current in tissue which it contacts,
   (ii) a means for inflating and maintaining the inflation of the balloon tip, and
   (iii) a means for supplying an electrical current to the balloon.

9. The method of claim 2 wherein the tip capable of heating comprises:
   a) a balloon capable of heating by circulation of a heated fluid within the balloon,
   b) a means for inflating and maintaining the inflation of the balloon, and
   c) a means for supplying a current of heated fluid to the balloon.

10. The method of claim 2 wherein the tip capable of heating comprises:
    a) a balloon capable of heating by internal absorption of electromagnetic radiation and conduction of the heat produced to the surface of the balloon,
    b) a means for inflating and maintaining the inflation of the balloon, and
    c) a means for supplying electromagnetic radiation to the balloon tip.

11. The method of claim 10 wherein the electromagnetic radiation is coherent or noncoherent light.

12. The method of claim 10 wherein the electromagnetic radiation is in the infrared range.

13. The method of 1 wherein step b) comprises maneuvering the heating portion into contact or close proximity with chordae tendineae of the mitral valve.

14. The method of claim 1 wherein step b) comprises maneuvering the heating portion into contact or close proximity with chordae tendineae of the tricuspid valve.

15. The method of claim 2 wherein the catheter has at least one means of moving the tip relative to the catheter.

16. The method of claim 15 wherein one means of moving the tip is a line connected to the tip of the catheter at its distal end, running within the catheter, and exiting the catheter at its proximal end.

17. The method of claim 2 wherein the tip system capable of heating heats by transmitting light to the chordae tendineae.

18. The method of claim 17 wherein the light is coherent light.

19. The method of claim 15 wherein one means of moving the tip comprises:
   a) a strip of one or more metals having the property of bending to a predetermined upon heating more than about 5° C. above a human's normal body temperature and returning to its original position upon cool to the normal temperature of a humans' body, and which is located longitudinally on the inner wall of the catheter, proximally to the tip of the catheter shaft;
   b) a heating means in contact with, or in close proximity to the strip of one or more metals;
   c) a remote, controllable source of energy capable of activating the heating means; and
   d) a means of transmitting energy from the source of energy to the heating means.

20. The method of claim 15 wherein the strip is composed of a memory metal.

21. The method of claim 15 wherein the strip is a bimetallic metal strip.

22. The device of claim 15 wherein the strip is composed of a memory metal.

23. The device of claim 15 wherein the strip is a bimetallic metal strip.

24. The method of claim 1 wherein step d) comprises causing the heating portion of the heating device to apply heat to the tissue conductively.

25. The method of claim 1 wherein step d) comprises causing the heating portion of the heating device to apply heat to the tissue radiantly.

26. The method of claim 1 wherein step d) comprises causing the heating portion of the heating device to apply heat to the tissue inductively.

* * * * *